(12) United States Patent
Christensen, IV et al.

(10) Patent No.: US 6,369,108 B1
(45) Date of Patent: Apr. 9, 2002

(54) METHOD FOR TREATING COPD

(75) Inventors: Siegfried B. Christensen, IV, Philadelphia; Theodore Torphy, Bryn Mawr, both of PA (US)

(73) Assignee: SmithKline Beecham Corporation, Philadelphia, PA (US)

( * ) Notice: Subject to any disclaimer, the term of this patent is extended or adjusted under 35 U.S.C. 154(b) by 0 days.

(21) Appl. No.: 09/582,739

(22) PCT Filed: Jan. 6, 1999

(86) PCT No.: PCT/US99/00214

§ 371 Date: Jun. 28, 2000

§ 102(e) Date: Jun. 28, 2000

(87) PCT Pub. No.: WO99/34798

PCT Pub. Date: Jul. 15, 1999

Related U.S. Application Data

(60) Provisional application No. 60/070,718, filed on Jan. 7, 1998, and provisional application No. 60/106,908, filed on Oct. 28, 1998.

(51) Int. Cl.$^7$ ............... A61K 31/165; A61K 31/192; A61K 31/216; A61K 31/30; A61K 31/4245

(52) U.S. Cl. ............... 514/567; 514/363; 514/364; 514/381; 514/530; 514/531; 514/538; 514/615; 514/619; 514/646

(58) Field of Search ............... 514/567, 363, 514/364, 381, 530, 531, 538, 615, 619, 646

(56) References Cited

U.S. PATENT DOCUMENTS 5,552,438 A    9/1996   Christensen ............... 514/520

OTHER PUBLICATIONS

Silvestre et al., Drugs Future, 23(6), 607–615 (1998) (abstract).*

* cited by examiner

*Primary Examiner*—Phyllis G. Spivack
(74) *Attorney, Agent, or Firm*—James M. Kanagy; Charles M. Kinzig

(57) ABSTRACT

A method for treating COPD is disclosed comprising administering compounds of Formula (I)

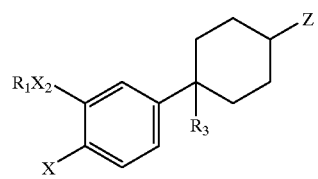

wherein the terms $R_1$, $R_3$, X, $X_2$ and Z are herein defined.

14 Claims, No Drawings

METHOD FOR TREATING COPD

This application claims benefit of provisional application Ser. No. 60/070,718 filed Jan. 7, 1998 and Ser. No. 60/106,908 filed Oct. 28, 1998.

FIELD OF THE INVENTION

The present invention relates to the use of certain compounds for treating chronic obstructive pulmonary disease (COPD).

BACKGROUND OF THE INVENTION

Chronic obstructive pulmonary disease (COPD) is an umbrella term frequently used to describe two conditions of fixed airways disease, chronic bronchitis and emphysema. Chronic bronchitis and emphysema are most commonly caused by smoking; approximately 90% of patients with COPD are or were smokers. Although approximately 50% of smokers develop chronic bronchitis, only 15% of smokers develop disabling airflow obstruction. Certain animals, particularly horses, suffer from COPD as well.

The airflow obstruction associated with COPD is progressive, may be accompanied by airway hyperreactivity, and may be partially reversible. Non-specific airway hyper-responsiveness may also play a role in the development of COPD and may be predictive of an accelerated rate of decline in lung function in smokers.

COPD is a significant cause of death and disability. It is currently the fourth leading cause of death in the United States and Europe. Treatment guidelines advocate early detection and implementation of smoking cessation programs to help reduce morbidity and mortality due to the disease. However, early detection and diagnosis has been difficult for a number of reasons.

COPD takes years to develop and smokers often deny any ill effects from smoking, attributing the early warning signs of increased breathlessness as a sign of age. Similarly, acute episodes of bronchitis often are not recognized by the general practitioner as early signs of COPD. Many patients exhibit features of more than one disease (e.g. chronic bronchitis or asthmatic bronchitis) making precise diagnosis a challenge, particularly in early disease. Also, many patients do not seek medical help until they are experiencing more severe symptoms associated with reduced lung function, such as dyspnea, persistent cough, and sputum production. As a consequence, the vast majority of patients are not diagnosed or treated until they are in a more advanced stage of disease.

There is a need for a new approach to treating COPD. This invention provides one such approach.

SUMMARY OF THE INVENTION

This invention covers a method for the prophylaxis or treatment of COPD in a mammal by administering to a mammal in need thereof an effective amount of a compound of Formula (I) alone or in admixture with a pharmaceutically acceptable excipient wherein Formula (I) comprises:

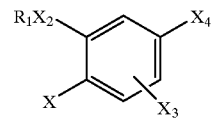

(I)

wherein:
$R_1$ is —$(CR_4R_5)_nC(O)O(CR_4R_5)_mR_6$, —$(CR_4R_5)_nC(O)NR_4(CR_4R_5)_mR_6$, —$(CR_4R_5)_nO(CR_4R_5)_mR_6$, or —$(CR_4R_5)_rR_6$ wherein the alkyl moieties may be optionally substituted with one or more halogens;
m is 0 to 2;
n is 1 to 4;
r is 0 to 6;
$R_4$ and $R_5$ are independently selected from hydrogen or a $C_{1-2}$ alkyl;
$R_6$ is hydrogen, methyl, hydroxyl, aryl, halo substituted aryl, aryloxy$C_{1-3}$ alkyl, halo substituted aryloxy$C_{1-3}$ alkyl, indanyl, indenyl, $C_{7-11}$ polycycloalkyl, tetrahydrofuranyl, furanyl, tetrahydropyranyl, pyranyl, tetrahydrothienyl, thienyl, tetrahydrothiopyranyl, thiopyranyl, $C_{3-6}$ cycloalkyl, or a $C_{4-6}$ cycloalkyl containing one or two unsaturated bonds, wherein the cycloalkyl and heterocyclic moieties may be optionally substituted by OH, 1 to 3 methyl groups or one ethyl group;
provided that:
a) when $R_6$ is hydroxyl, then m is 2; or
b) when $R_6$ is hydroxyl, then r is 2 to 6; or
c) when $R_6$ is 2-tetrahydropyranyl, 2-tetrahydrothiopyranyl, 2-tetrahydrofuranyl, or 2-tetrahydrothienyl, then m is 1 or 2; or
d) when $R_6$ is 2-tetrahydropyranyl, 2-tetrahydrothiopyranyl, 2-tetrahydrofuranyl, or 2-tetrahydrothienyl, then r is 1 to 6;
e) when n is 1 and m is 0, then $R_6$ is other than H in —$(CR_4R_5)_nO(CR_4R_5)_mR_6$;
X is $YR_2$, halogen, nitro, $NR_4R_5$, or formyl amine;
Y is O or $S(O)_{m'}$;
m' is 0, 1, or 2;
$X_2$ is O or $NR_8$;
$X_3$ is hydrogen or X;
$X_4$ is

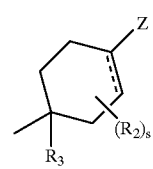

(a)

or

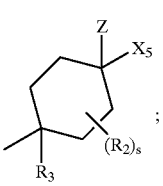

(b)

$X_5$ is H, $R_9$, $OR_8$, CN, $C(O)R_8$, $C(O)OR_8$, $C(O)NR_8R_8$, or $NR_8R_8$;

$R_2$ is independently selected from the group consisting of —$CH_3$ and —$CH_2CH_3$ optionally substituted by 1 or more halogens;

s is 0 to 4;

$R_3$ is hydrogen, halogen, $C_{1-4}$ alkyl, $CH_2NHC(O)C(O)NH_2$, halo-substituted $C_{1-4}$ alkyl, —CH=$CR_8R_{8'}$, cyclopropyl optionally substituted by $R_{8'}$, CN, $OR_8$, $CH_2OR_8$, $NR_8R_{10}$, $CH_2NR_8R_{10}$, $C(Z')H$, $C(O)OR_8$, $C(O)NR_8R_{10}$, or C≡$CR_{8'}$;

Z' is O, $NR_9$, $NOR_8$, NCN, C(—CN)$_2$, $CR_8CN$, $CR_8NO_2$, $CR_8C(O)OR_8$, $CR_8C(O)NR_8R_8$, C(—CN)$NO_2$, C(—CN)C(O)$OR_9$, or C(—CN)C(O)$NR_8R_8$;

Z is $C(Y')R_{14}$, $C(O)OR_{14}$, $C(Y')NR_{10}R_{14}$, $C(NR_{10})NR_{10}R_{14}$, CN, $C(NOR_8)R_{14}$, $C(O)NR_8NR_8C(O)R_8$, $C(O)NR_8NR_{10}R_{14}$, $C(NOR_{14})R_8$, $C(NR_8)NR_{10}R_{14}$, $C(NR_{14})NR_8R_8$, $C(NCN)NR_{10}R_{14}$, $C(NCN)SR_9$, (2-, 4- or 5-imidazolyl), (3-, 4- or 5-pyrazolyl), (4- or 5-triazolyl[1,2,3]), (3- or 5-triazolyl[1,2,4]), (5-tetrazolyl), (2-, 4- or 5-oxazolyl), (3-, 4- or 5-isoxazolyl), (3- or 5-oxadiazolyl[1,2,4]), (2-oxadiazolyl[1,3,4]), (2-thiadiazolyl[1,3,4]), (2-, 4-, or 5-thiazolyl), (2-, 4-, or 5-oxazolidinyl), (2-, 4-, or 5-thiazolidinyl), or (2-, 4-, or 5-imidazolidinyl); wherein all of the heterocylic ring systems may be optionally substituted one or more times by $R_{14}$;

the dotted line in formula (a) represents a single or double bond;

Y' is O or S;

$R_7$ is —$(CR_4R_5)_qR_{12}$ or $C_{1-6}$ alkyl wherein the $R_{12}$ or $C_{1-6}$ alkyl group is optionally substituted one or more times by $C_{1-2}$ alkyl optionally substituted by one to three fluorines, —F, —Br, —Cl, —$NO_2$, —$NR_{10}R_{11}$, —$C(O)R_8$, —$C(O)OR_8$, —$OR_8$, —CN, —$C(O)NR_{10}R_{11}$, —$OC(O)NR_{10}R_{11}$, —$OC(O)R_8$, —$NR_{10}C(O)NR_{10}R_{11}$, —$NR_{10}C(O)R_{11}$, —$NR_{10}C(O)OR_9$, —$NR_{10}C(O)R_{13}$, —$C(NR_{10})NR_{10}R_{11}$, —C(NCN)$NR_{10}R_{11}$, —$C(NCN)SR_9$, —$NR_{10}C(NCN)SR_9$, —$NR_{10}C(NCN)NR_{10}R_{11}$, —$NR_{10}S(O)_2R_9$, —$S(O)_mR_9$, —$NR_{10}C(O)C(O)NR_{10}R_{11}$, —$NR_{10}C(O)C(O)R_{10}$, thiazolyl, imidazolyl, oxazolyl, pyrazolyl, triazolyl, or tetrazolyl;

q is 0, 1, or 2;

$R_{12}$ is $C_{3-7}$ cycloalkyl, (2-, 3- or 4-pyridyl), pyrimidyl, pyrazolyl, (1- or 2-imidazolyl), thiazolyl, triazolyl, pyrrolyl, piperazinyl, piperidinyl, morpholinyl, furanyl, (2- or 3-thienyl), (4- or 5-thiazolyl), quinolinyl, naphthyl, or phenyl;

$R_8$ is independently selected from hydrogen or $R_9$;

$R_8'$ is $R_8$ or fluorine;

$R_9$ is $C_{1-4}$ alkyl optionally substituted by one to three fluorines;

$R_{10}$ is $OR_8$ or $R_{11}$;

$R_{11}$ is hydrogen, or $C_{1-4}$ alkyl optionally substituted by one to three fluorines; or when $R_{10}$ and $R_{11}$ are as $NR_{10}R_{11}$ they may together with the nitrogen form a 5 to 7 membered ring optionally containing at least one additional heteroatom selected from O, N, or S;

$R_{13}$ is oxazolidinyl, oxazolyl, thiazolyl, pyrazolyl, triazolyl, tetrazolyl, imidazolyl, imidazolidinyl, thiazolidinyl, isoxazolyl, oxadiazolyl, or thiadiazolyl, and each of these heterocyclic rings is connected through a carbon atom and each may be unsubstituted or substituted by one or two $C_{1-2}$ alkyl groups;

$R_{14}$ is hydrogen or $R_7$; or when $R_{10}$ and $R_{14}$ are as $NR_{10}R_{14}$ they may together with the nitrogen form a 5 to 7 membered ring optionally containing one or more additional heteroatoms selected from O, N, or S;

provided that:

f) when $R_{12}$ is N-pyrazolyl, N-imnidazolyl, N-triazolyl, N-pyrrolyl, N-piperazinyl, N-piperidinyl, or N-morpholinyl, then q is not 1; or g) when $X_2R_1$ is $OCF_2H$ or $OCF_3$, X is $OCF_2H$ or $OCF_3$, $X_3$ is H, s is zero, $X_5$ is H, Z is $C(O)OR_{14}$ and $R_{14}$ is $C_{1-7}$ unsubstituted alkyl, then $R_3$ is other than H;

or the pharmaceutically acceptable salts thereof.

In a second aspect, this invention relates to the use of a compound of Formula (II) for treating COPD in a mammal, particularly a human, wherein Formula (II) is defined as follows:

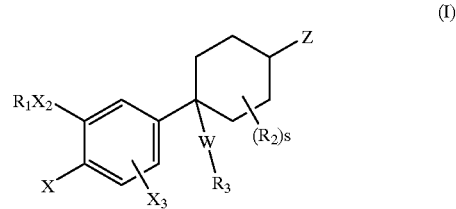

(I)

wherein:

$R_1$ is —$(CR_4R_5)_nC(O)O(CR_4R_5)_mR_6$, —$(CR_4R_5)_nC(O)NR_4(CR_4R_5)_mR_6$, —$(CR_4R_5)_nO(CR_4R_5)_mR_6$, or —$(CR_4R_5)_rR_6$ wherein the alkyl moieties unsubstituted or substituted with one or more halogens;

m is 0 to 2;

n is 0 to 4;

r is 0 to 6;

$R_4$ and $R_5$ are independently selected hydrogen or $C_{1-2}$ alkyl;

$R_6$ is hydrogen, methyl, hydroxyl, aryl, halo substituted aryl, aryloxy$C_{1-3}$ alkyl, halo substituted aryloxy$C_{1-3}$ alkyl, indanyl, indenyl, $C_{7-11}$ polycycloalkyl, tetrahydrofuranyl, furanyl, tetrahydropyranyl, pyranyl, tetrahydrothienyl, thienyl, tetrahydrothiopyranyl, thiopyranyl, $C_{3-6}$ cycloalkyl, or a $C_{4-6}$ cycloalkyl containing one or two unsaturated bonds, wherein the cycloalkyl or heterocyclic moiety is unsubstituted or substituted by 1 to 3 methyl groups, one ethyl group, or an hydroxyl group;

provided that:

a) when $R_6$ is hydroxyl, then m is 2; or b) when $R_6$ is hydroxyl, then r is 2 to 6; or c) when $R_6$ is 2-tetrahydropyranyl, 2-tetrahydrothiopyranyl, 2-tetrahydrofuranyl, or 2-tetrahydrothienyl, then m is 1 or 2; or d) when $R_6$ is 2-tetrahydropyranyl, 2-tetrahydrothiopyranyl, 2-tetrahydrofuranyl, or 2-tetrahydrothienyl, then r is 1 to 6;

e) when n is 1 and m is 0, then $R_6$ is other than H in —$(CR_4R_5)_nO(CR_4R_5)_mR_6$;

X is $YR_2$, fluorine, $NR_4R_5$, or formyl amine;

Y is O or $S(O)_{m'}$;

m' is 0, 1, or 2;

$X_2$ is O or $NR_8$;

$X_3$ is hydrogen or X;

$X_4$ is H, $R_9$, $OR_8$, CN, $C(O)R_8$, $C(O)OR_8$, $C(O)NR_8R_8$, or $NR_8R_8$;

$R_2$ is independently selected from —$CH_3$ or —$CH_2CH_3$ optionally substituted by 1 or more halogens;

s is 0 to 4;

W is alkyl of 2 to 6 carbons, alkenyl of 2 to 6 carbon atoms or alkynyl of 2 to 6 carbon atoms;

$R_3$ is $COOR_{14}$, $C(O)NR_4R_{14}$ or $R_7$;

Z is $OR_{14}$, $OR_{15}$, $SR_{14}$, $S(O)_m R_7$, $S(O)_2 NR_{10}R_{14}$, $NR_{10}R_{14}$, $NR_{14}C(O)R_9$, $NR_{10}C(Y')R_{14}$, $NR_{10}C(O)OR_7$, $NR_{10}C(Y')NR_{10}R_{14}$, $NR_{10}S(O)_2 NR_{10}R_{14}$, $NR_{10}C(NCN)NR_{10}R_{14}$, $NR_{10}S(O)_2 R_7$, $NR_{10}C(CR_4NO_2)NR_{10}R_{14}$, $NR_{10}C(NCN)SR_9$, $NR_{10}C(CR_4NO_2)SR_9$, $NR_{10}C(NR_{10})NR_{10}R_{14}$, $NR_{10}C(O)C(O)NR_{10}R_{14}$, or $NR_{10}C(O)C(O)OR_{14}$;

Y' is O or S;

$R_7$ is $—(CR_4R_5)_q R_{12}$ or $C_{1-6}$ alkyl wherein the $R_{12}$ or $C_{1-6}$ alkyl group is unsubstituted or substituted one or more times by methyl or ethyl unsubstituted or substituted by 1-3 fluorines, —F, —Br, —Cl, —$NO_2$, —$NR_{10}R_{11}$, —$C(O)R_8$, —$CO_2R_8$, —$O(CH_2)_{2-4}OR_8$, —$O(CH_2)_q R_8$, —CN, —$C(O)NR_{10}R_{11}$, —$O(CH_2)_q C(O)NR_{10}R_{11}$, —$O(CH_2)_q C(O)R_9$, —$NR_{10}C(O)NR_{10}R_{11}$, —$NR_{10}C(O)R_{11}$, —$NR_{10}C(O)OR_9$, —$NR_{10}C(O)R_{13}$, —$C(NR_{10})NR_{10}R_{11}$, —$C(NCN)NR_{10}R_{11}$, —$C(NCN)SR_9$, —$NR_{10}C(NCN)SR_9$, —$NR_{10}C(NCN)NR_{10}R_{11}$, —$NR_{10}S(O)_2 R_9$, —$S(O)_m R_9$, —$NR_{10}C(O)C(O)NR_{10}R_{11}$, —$NR_{10}C(O)C(O)R_{10}$, or $R_{13}$;

q is 0, 1, or 2;

$R_{12}$ is $R_{13}$, $C_3$–$C_7$ cycloalkyl, or an unsubstituted or substituted aryl or heteroaryl group selected from the group consisting of (2-, 3- or 4-pyridyl), pyrimidinyl, pyrazolyl, (1- or 2-imidazolyl), pyrrolyl, piperazinyl, piperidinyl, morpholinyl, furanyl, (2- or 3-thienyl), quinolinyl, naphthyl, and phenyl;

$R_8$ is independently selected from hydrogen or $R_9$;

$R_9$ is $C_{1-4}$ alkyl optionally substituted by one to three fluorines;

$R_{10}$ is $OR_8$ or $R_{11}$;

$R_{11}$ is hydrogen, or $C_{1-4}$ alkyl unsubstituted or substituted by one to three fluorines; or when $R_{10}$ and $R_{11}$ are as $NR_{10}R_{11}$ they may together with the nitrogen form a 5 to 7 membered ring comprised of carbon or carbon and one or more additional heteroatoms selected from O, N, or S;

$R_{13}$ is a substituted or unsubstituted heteroaryl group selected from the group consisting of oxazolidinyl, oxazolyl, thiazolyl, pyrazolyl, triazolyl, tetrazolyl, imidazolyl, imidazolidinyl, thiazolidinyl, isoxazolyl, oxadiazolyl, and thiadiazolyl, and where $R_{13}$ is substituted on $R_{12}$ or $R_{13}$ the rings are connected through a carbon atom and each second $R_{13}$ ring may be unsubstituted or substituted by one or two $C_{1-2}$ alkyl groups unsubstituted or substituted on the methyl with 1 to 3 fluoro atoms;

$R_{14}$ is hydrogen or $R_7$; or when $R_8$ and $R_{14}$ are as $NR_8R_{14}$ they may together with the nitrogen form a 5 to 7 membered ring comprised of carbon or carbon and one or more additional heteroatoms selected from O, N, or S;

$R_{15}$ is $C(O)R_{14}$, $C(O)NR_8R_{14}$, $S(O)_q NR_8R_{14}$ or $S(O)_q R_7$ where q is 0, 1 or 2;

provided that:

(f) $R_7$ is not $C_{1-4}$ alkyl unsubstituted or substituted by one to three fluorines;

or the pharmaceutically acceptable salts thereof.

In a further aspect, this invention relates to a pharmaceutically acceptable composition for treating COPD comprising a pharmaceutically acceptable excipient and between about 1 and 60 mg of a compound of Formula (I) or (II) at least once daily.

DETAILED DESCRIPTION OF THE INVENTION

This invention relates to the use of compounds of Formulas (I) or (II) and to pharmaceutical compositions comprising a compound of Formulas (I) or (II) and a pharmaceutically acceptable carrier or diluent, for treating COPD in a mammal, particularly a human, suffering from COPD. The drug may have use in the prophylaxis of the phenomena associated with COPD before clinical manifestation of the disease in a mammal, particularly a human.

COPD is characterized by a chronic inflammatory process in the lung marked by in increase in the activation and/or number of alveolar macrophages, $CD8^+$ T-cells and neutrophils. Most notably with respect to the therapy of COPD is the ability to alter the trafficking and activation of neutrophils. The neutrophil is believed to play a central role in the pathophysiology of COPD. Neutrophil activation results in the release of a number of inflammatory mediators and proteinases, most importantly neutrophil elastase which contributes to the progressive fibrosis, airway stenosis and destruction of the lung parenchyma, leading to an accelerated decline in airway function. Neutrophil elastase is also a powerful mucus secretagogue and thus may contribute to the characteristic mucus hypersecretion that characterizes COPD. The compounds of this invention have marked effects on neutrophil activity, inhibiting neutrophil chemotaxis and degranulation in vitro. In animal models, the instant compounds reduce neutrophil extravasation from the circulation, pulmonary sequestration and the edematous responses to a number inflammatory insults in vivo.

Additional activities that may contribute to the therapeutic activity of PDE4 inhibitors in COPD include bronchodilation and modulation of pulmonary neuronal activity. Although the degree of reversibility of reduced airway flow is low in COPD, a small increase may have an acute positive effect, as well as a gradual reduction in the slope of the decline which may result in a profound effect on quality of life for COPD patients. The ability of inhaled muscarinc antagonists to produce clinically meaningful improvements in pulmonary function in COPD, at least acutely, suggest that a large component of the reversible airways obstruction in this disease is associated with a dysregulation of pulmonary nerves. Although not studied in detail as yet, PDE4 inhibitors may also modulate the activity of airway epithelial cells, a rich source of proinflammatory mediators that are released upon environmental insult (e.g., smoke), and inhibit vascular smooth muscle hyperplasia, a structural change in end stage COPD that is associated with right heart failure.

The preferred compounds for use in this invention are defined as follows:

When $R_1$ for the compounds of the Formula (I) is an alkyl substituted by 1 or more halogens, the halogens are preferably fluorine and chlorine, more preferably a $C_{1-4}$ alkyl substituted by 1 or more fluorines. The preferred halosubstituted alkyl chain length is one or one two carbons, and most preferred are the moieties —$CF_3$, —$CH_2F$, —$CHF_2$, —$CF_2CHF_2$, —$CH_2CF_3$, and —$CH_2CHF_2$. Preferred $R_1$ substitutents for the compounds of the Formula (I) are $CH_2$-cyclopropyl, $CH_2$—$C_{5-6}$ cycloalkyl, $C_{4-6}$ cycloalkyl, $C_{7-11}$ polycycloalkyl, (3- or 4-cyclopentenyl), phenyl, tetrahydrofuran-3-yl, benzyl or $C_{1-2}$ alkyl optionally substituted by 1 or more fluorines, —$(CH_2)_{1-3}C(O)O(CH_2)_{0-2}CH_3$, —$(CH_2)_{1-3}O(CH_2)_{0-2}CH_3$, and —$(CH_2)_{2-4}OH$.

When the $R_1$ term contains the moiety $(CR_4R_5)$, the $R_4$ and $R_5$ terms are independently hydrogen or alkyl. This allows for branching of the individual methylene units as $(CR_4R_5)_n$ or $(CR_4R_5)_m$; each repeating methylene unit is independent of the other, e.g., $(CR_4R_5)_n$ wherein n is 2 can be —$CH_2CH$(—$CH_3$)—, for instance. The individual hydrogen atoms of the repeating methylene unit or the branching hydrocarbon can optionally be substituted by fluorine independent of each other to yield, for instance, the preferred $R_1$ substitutions, as noted above.

When $R_1$ is a $C_{7-11}$ polycycloalkyl, examples are bicyclo [2.2.1]-heptyl, bicyclo[2.2.2]octyl, bicyclo[3.2.1]octyl, tricyclo[5.2.1.0$^{2.6}$]decyl, etc. additional examples of which are described in Saccamano et al., WO 87/06576, published Nov. 5, 1987, whose disclosure is incorporated herein by reference in its entirety.

Z is preferably $C(O)R_8$, $C(O)OR_8$, $C(O)NR_8R_8$, $C(NR_8)NR_8R_8$, CN, $C(NOR_8)R_8$, $C(O)NR_8NR_8C(O)R_8$, $C(NR_8)NR_8R_8$, $C(NCN)NR_8R_8$, $C(NCN)SR_9$, (1-, 4- or 5-$\{R_8\}$-2-imidazolyl), (1-, 4- or 5-$\{R_8\}$-3-pyrazolyl), (1-, 2- or 5-$\{R_8\}$-4-triazolyl[1,2,3]), (1-, 2-, 4- or 5-$\{R_8\}$-3-triazolyl [1,2,4]), (1- or 2-$\{R_8\}$-5-tetrazolyl), (4- or 5-$\{R_8\}$-2-oxazolyl), (3- or 4-$\{R_8\}$-5-isoxazolyl), (3-$\{R_8\}$-5-oxadiazolyl[1,2,4]), (5-$\{R_8\}$-3-oxadiazolyl[1,2,4]), (5-$\{R_8\}$-2-oxadiazolyl[1,3,4]), (5-$\{R_8\}$-2-thiadiazolyl[1,3,4]), (4- or 5-$\{R_8\}$-2-thiazolyl), (4- or 5-$\{R_8\}$-2-oxazolidinyl), (4- or 5-$\{R_8\}$-2-thiazolidinyl), (1-, 4- or 5-$\{R_8\}$-2-imidazolidinyl); most preferred are those compounds wherein the $R_8$ group of Z is $R_4$.

$X_5$ is preferably hydrogen, $C_{1-2}$ alkyl optionally substituted by one to three fluorines, $OR_8$, CN, $C(O)R_8$, $C(O)OR_8$, $C(O)NR_8R_8$, or $NR_8R_8$.

Preferred X groups for Formula (I) are those wherein X is $YR_2$ and Y is oxygen. The preferred $X_2$ group for Formula (I) is that wherein $X_2$ is oxygen. The preferred $X_3$ group for Formula (I) is that wherein $X_3$ is hydrogen. Preferred $R_2$ groups, where applicable, are $C_{1-2}$ alkyl optionally substituted by 1 or more halogens. The halogen atoms are preferably fluorine and chlorine, more preferably fluorine. More preferred $R_2$ groups are those wherein $R_2$ is methyl, or the fluoro-substituted alkyls, specifically a $C_{1-2}$ alkyl, such as a —$CF_3$, —$CHF_2$, or —$CH_2CHF_2$ moiety. Most preferred are the —$CHF_2$ and —$CH_3$ moieties.

Preferred $R_3$ moieties are $C(O)NH_2$, $C\equiv CR_8$, CN, C(Z') H, $CH_2OH$, $CH_2F$, $CF_2H$, and $CF_3$. More preferred are —$C\equiv CH$ and CN. Z' is preferably O or $NOR_8$.

Preferred $R_7$ moieties include optionally substituted —$(CH_2)_{1-2}$(cyclopropyl), —$(CH_2)_{0-2}$(cyclobutyl), —$(CH_2)_{0-2}$(cyclopentyl), —$(CH_2)_{0-2}$(cyclohexyl), —$(CH_2)_{0-2}$(2-, 3- or 4-pyridyl), —$(CH_2)_{1-2}$(2-imidazolyl), —$(CH_2)_2$(4-morpholinyl), —$(CH_2)_2$(4-piperazinyl), —$(CH_2)_{1-2}$(2-thienyl), —$(CH_2)_{1-2}$(4-thiazolyl), and —$(CH_2)_{0-2}$phenyl;

Preferred rings when $R_{10}$ and $R_{11}$ in the moiety —$NR_{10}R_{11}$ together with the nitrogen to which they are attached form a 5 to 7 membered ring optionally containing at least one additional heteroatom selected from O, N, or S include, but are not limited to 1-imidazolyl, 2-($R_8$)-1-imidazolyl, 1-pyrazolyl, 3-($R_8$)-1-pyrazolyl, 1-triazolyl, 2-triazolyl, 5-($R_8$)-1-triazolyl, 5-($R_8$)-2-triazolyl, 5-($R_8$)-1-tetrazolyl, 5-($R_8$)-2-tetrazolyl, 1-tetrazolyl, 2-tetrazloyl, morpholinyl, piperazinyl, 4-($R_8$)-1-piperazinyl, or pyrrolyl ring.

Preferred rings when $R_{10}$ and $R_{14}$ in the moiety —$NR_{10}R_{14}$ together with the nitrogen to which they are attached may form a 5 to 7 membered ring optionally containing at least one additional heteroatom selected from O, N, or S include, but are not limited to 1-imidazolyl, 1-pyrazolyl, 1-triazolyl, 2-triazolyl, 1-tetrazolyl, 2-tetrazolyl, morpholinyl, piperazinyl, and pyrrolyl. The respective rings may be additionally substituted, where applicable, on an available nitrogen or carbon by the moiety $R_7$ as described herein for Formula (I). Illustrations of such carbon substitutions includes, but are not limited to, 2-($R_7$)-1-imidazolyl, 4-($R_7$)-1-imidazolyl, 5-($R_7$)-1-imidazolyl, 3-($R_7$)-1-pyrazolyl, 4-($R_7$)-1-pyrazolyl, 5-($R_7$)-1-pyrazolyl, 4-($R_7$)-2-triazolyl, 5-($R_7$)-2-triazolyl, 4-($R_7$)-1triazolyl, 5-($R_7$)-1-triazolyl, 5-($R_7$)-1-tetrazolyl, and 5-($R_7$)-2-tetrazolyl. Applicable nitrogen substitution by $R_7$ includes, but is not limited to, 1-($R_7$)-2-tetrazolyl, 2-($R_7$)-1-tetrazolyl, 4-($R_7$)-1-piperazinyl. Where applicable, the ring may be substituted one or more times by $R_7$.

Preferred groups for $NR_{10}R_{14}$ which contain a heterocyclic ring are 5-($R_{14}$)-1-tetrazolyl, 2-($R_{14}$)-1-imidazolyl, 5-($R_{14}$)-2-tetrazolyl, or 4-($R_{14}$)-1-piperazinyl.

Preferred rings for $R_{13}$ include (2-, 4- or 5-imidazolyl), (3-, 4- or 5-pyrazolyl), (4- or 5-triazolyl[1,2,3]), (3- or 5-triazolyl[1,2,4]), (5-tetrazolyl), (2-, 4- or 5-oxazolyl), (3-, 4- or 5-isoxazolyl), (3- or 5-oxadiazolyl[1,2,4]), (2-oxadiazolyl[1,3,4]), (2-thiadiazolyl[1,3,4]), (2-, 4-, or 5-thiazolyl), (2-, 4-, or 5-oxazolidinyl), (2-, 4-, or 5-thiazolidinyl), or (2-, 4-, or 5-imidazolidinyl).

When the $R_7$ group is optionally substituted by a heterocyclic ring such as imidazolyl, pyrazolyl, triazolyl, tetrazolyl, or thiazolyl, the heterocyclic ring itself may be optionally substituted by $R_8$ either on an available nitrogen or carbon atom, such as 1-($R_8$)-2-imidazolyl, 1-($R_8$)-4-imidazolyl, 1-($R_8$)-5-imidazolyl, 1-($R_8$)-3-pyrazolyl, 1-($R_8$)-4-pyrazolyl, 1-($R_8$)-5-pyrazolyl, 1-($R_8$)-4-triazoly, or 1-($R_8$)-5-triazolyl. Where applicable, the ring may be substituted one or more times by $R_8$.

Preferred are those compounds of the Formula (I) wherein $R_1$ is —$CH_2$-cyclopropyl, —$CH_2$—$C_{5-6}$ cycloalkyl, —$C_{4-6}$ cycloalkyl, tetrahydrofuran-3-yl, (3- or 4-cyclopentenyl), benzyl or —$C_{1-2}$ alkyl optionally substituted by 1 or more fluorines, and —$(CH_2)_{2-4}$ OH; $R_2$ is methyl or fluoro-substituted alkyl, $R_3$ is CN or $C\equiv CR_8$; and X is $YR_2$.

Most preferred are those compounds wherein $R_1$ is —$CH_2$-cyclopropyl, cyclopentyl, methyl or $CF_2H$; $R_3$ is CN; X is $YR_2$; Y is oxygen; $X_2$ is oxygen; $X_3$ is hydrogen; and $R_2$ is $CF_2H$ or methyl.

A preferred subgenus of the compounds of the Formula (I) is the compounds of the Formula (Ia)

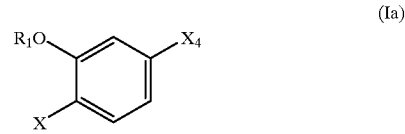

(Ia)

wherein:

$R_1$ is $CH_2$-cyclopropyl, $CH_2$—$C_{5-6}$ cycloalkyl optionally substituted by OH, $C_{4-6}$ cycloalkyl, $C_{7-11}$ polycycloalkyl, (3- or 4-cyclopentenyl), phenyl, tetrahydrofuran-3-yl, benzyl or $C_{1-2}$ alkyl optionally substituted by 1 or more fluorines,—$(CH_2)_{1-3}C(O)O(CH_2)_{0-2}CH_3$, —$(CH_2)_{1-3}O(CH_2)_{0-2}CH_3$, and —$(CH_2)_{2-4}OH$;

X is $YR_2$, halogen, nitro, $NR_4R_5$, or formyl amine;

$X_4$ is

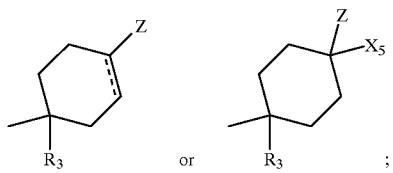

$X_5$ is H, $R_9$, $OR_8$, CN, $C(O)R_8$, $C(O)OR_8$, $C(O)NR_8R_8$, or $NR_8R_8$;

Y is O or $S(O)_{m'}$;

m' is 0, 1, or 2;

$R_2$ is —$CH_3$ or —$CH_2CH_3$ optionally substituted by 1 or more halogens;

$R_3$ is hydrogen, $C_{1-4}$ alkyl, $CH_2NHC(O)C(O)NH_2$, halo-substituted $C_{1-4}$ alkyl, CN, $CH_2OR_8$, C(Z')H, C(O)$OR_8$, $C(O)NR_8R_{10}$, or C≡$CR_8$;

Z' is O or $NOR_8$;

Z is $C(O)R_{14}$, $C(O)OR_{14}$, $C(O)NR_{10}R_{14}$, $C(NR_{10})NR_{10}R_{14}$, CN, $C(NOR_8)R_{14}$, $C(O)NR_8NR_8C(O)R_8$, $C(O)NR_8NR_{10}R_{14}$, $C(NOR_{14})R_8$, $C(NR_8)NR_{10}R_{14}$, $C(NR_{14})NR_8R_8$, $C(NCN)NR_{10}R_{14}$, $C(NCN)SR_9$, (1-, 4- or 5-{$R_{14}$}-2-imidazolyl), (1-, 4- or 5-{$R_{14}$}-3-pyrazolyl), (1-, 2- or 5-{$R_{14}$}-4-triazolyl[1,2,3]), (1-, 2-, 4- or 5-{$R_{14}$}-3-triazolyl[1,2,4]), (1- or 2-{$R_{14}$}-5-tetrazolyl), (4- or 5-{$R_{14}$}-2-oxazolyl), (3- or 4-{$R_{14}$}-5-isoxazolyl), (3-{$R_{14}$}-5-oxadiazolyl[1,2,4]), (5-{$R_{14}$}-3-oxadiazolyl[1,2,4]), (5-{$R_{14}$}-2-oxadiazolyl[1,3,4]), (5-{$R_{14}$}-2-thiadiazolyl[1,3,4]), (4- or 5-{$R_{14}$}-2-thiazolyl), (4- or 5-{$R_{14}$}-2-oxazolidinyl), (4- or 5-{$R_{14}$}-2-thiazolidinyl), (1-, 4- or 5- {$R_{14}$}-2-imidazolidinyl);

$R_7$ is —$(CR_4R_5)_qR_{12}$ or $C_{1-6}$ alkyl wherein the $R_{12}$ or $C_{1-6}$ alkyl group is optionally substituted one or more times by $C_{1-2}$ alkyl optionally substituted by one to three fluorines, —F, —Br, —Cl, —$NO_2$, —$NR_{10}R_{11}$, —$C(O)R_8$, —$C(O)OR_8$, —$OR_8$, —CN, —$C(O)NR_{10}R_{11}$, —$OC(O)NR_{10}R_{11}$, —$OC(O)R_8$, —$NR_{10}C(O)NR_{10}R_{11}$, —$NR_{10}C(O)R_{11}$, —$NR_{10}C(O)OR_9$, —$NR_{10}C(O)R_{13}$, —$C(NR_{10})NR_{10}R_{11}$, —C(NCN)$NR_{10}R_{11}$, —$C(NCN)SR_9$, —$NR_{10}C(NCN)SR_9$, —$NR_{10}C(NCN)NR_{10}R_{11}$, —$NR_{10}S(O)_2R_9$, —$S(O)_{m'}R_9$, —$NR_{10}C(O)C(O)NR_{10}R_{11}$, —$NR_{10}C(O)C(O)R_{10}$, thiazolyi, imidazolyl, oxazolyl, pyrazolyl, triazolyl, or tetrazolyl;

q is 0, 1, or 2;

$R_{12}$ is $C_3$-$C_7$ cycloalkyl, (2-, 3- or 4-pyridyl), (1- or 2-imidazolyl), piperazinyl, morpholinyl, (2- or 3-thienyl), (4- or 5-thiazolyl), or phenyl;

the dotted line formula (a) represents a single or double bond;

$R_8$ is independently selected from hydrogen or $R_9$;

$R_9$ is $C_{1-4}$ alkyl optionally substituted by one to three fluorines;

$R_{10}$ is $OR_8$ or $R_{11}$;

$R_{11}$ is hydrogen or $C_{1-4}$ alkyl optionally substituted by one to three fluorines; or when $R_{10}$ and $R_{11}$ are as $NR_{10}R_{11}$ they may together with the nitrogen form a 5 to 7 membered ring optionally containing at least one additional heteroatom selected from O, N, or S;

$R_{13}$ is oxazolidinyl, oxazolyl, thiazolyl, pyrazolyl, triazolyl, tetrazolyl, imidazolyl, imidazolidinyl, thiazolidinyl, isoxazolyl, oxadiazolyl, or thiadiazolyl, and each of these heterocyclic rings is connected through a carbon atom and each may be unsubstituted or substituted by one or two $C_{1-2}$ alkyl groups;

$R_{14}$ is hydrogen or $R_7$; or when $R_{10}$ and $R_{14}$ are as $NR_{10}R_{14}$ they may together with the nitrogen form a 5 to 7 membered ring optionally containing one or more additional heteroatoms selected from O, N, or S;

provided that:
a) when $R_{12}$ is N-imidazolyl, N-triazolyl, N-pyrrolyl, N-piperazinyl, or N-morpholinyl, then q is not 1; or
b) when $R_1$ is $CF_2H$ or $CF_3$, X is F, $OCF_2H$, or $OCF_3$, $X_5$ is H, Z is $C(O)OR_{14}$ and $R_{14}$ is $C_{1-7}$ unsubstituted alkyl, then $R_3$ is other than H;

or the pharmaceutically acceptable salts thereof.

The most perferred compounds of Formula (I) are:

methyl 4-cyano-4-(3-cyclopentyloxy-4-methoxyphenyl) cyclohex-1-ene-1-carboxylate;

4-cyano-4-(3-cyclopentyloxy-4-methoxyphenyl)cyclohex-1-ene-1-carboxylic acid;

methyl cis-[4-cyano-4-(3-cyclopentyloxy-4-methoxyphenyl)cyclohexane-1-carboxylate];

methyl trans-[4-cyano-4-(3-cyclopentyloxy4-methoxyphenyl)cyclohexane-1-carboxylate];

methyl cis-[4-(3,4-bisdifluoromethoxyphenyl)-4-cyanocyclohexane-1-carboxylate];

methyl trans-[4-(3,4-bisdifluoromethoxyphenyl)-4-cyanocyclohexane-1-carboxylate];

cis-[4-cyano-4-(3-cyclopentyloxy-4-methoxyphenyl) cyclohexane-1-carboxylic acid];

cis-[4-cyano-4-(3-cyclopentyloxy-4-methoxyphenyl) cyclohexane-1-carboxylate], tris(hydroxymethyl) ammonium methane salt;

cis-[4-(3,4-bisdifluoromethoxyphenyl)-4-cyanocyclohexane-1-carboxylic acid];

trans-[4-cyano-4-(3-cyclopentyloxy-4-methoxyphenyl) cyclohexane-1-carboxylic acid];

cis-[4-cyano-4-(3-cyclopropylmethoxy-4-methoxyphenyl) cyclohexane-1-carboxylic acid];

trans-[4-cyano-4-(3-cyclopropylmethoxy-4-methoxyphenyl)cyclohexane-1-carboxylic acid];methyl cis-[4-cyano-4-(3-cyclopropylmethoxy-4-methoxyphenyl)cyclohexane-1-carboxylate];

methyl trans-[4-cyano-4-(3-cyclopropylmethoxy-4-methoxyphenyl)cyclohexane-1-carboxylate];

methyl cis-[4-cyano-4-(3-cyclopropylmethoxy-4-difluoromethoxyphenyl)cyclohexane-1-carboxylate];

methyl trans-[4-cyano-4-(3-cyclopropylmethoxy-4-difluoromethoxyphenyl)cyclohexane-1-carboxylate];

cis-[4-cyano-4-(3-cyclopropylmethoxy-4-difluoromethoxyphenyl)cyclohexane-1-carboxylic acid];

trans-[4-cyano-4-(3-cyclopropylmethoxy-4-difluoromethoxyphenyl)cyclohexane-1-carboxylic acid];

cis-[4-cyano-4-(3-cyclopentyloxy-4-methoxyphenyl) cyclohexane-1-carboxamide];

cis-[4-cyano-4-(3,4-bisdifluoromethoxyphenyl) cyclohexane-1-carboxamide];

trans-[4-cyano-4-(3,4-bisdifluoromethoxyphenyl) cyclohexane-1-carboxainide];

cis-[4-cyano-4-(3,4-bisdifluoromethoxyphenyl) cyclohexane-1-carbohydrazide];

cis-[4-cyano-4-(3,4-bisdifluoromethoxyphenyl) cyclohexane-1-(2-acetylcarbohydrazide)];

cis-{4-(3,4-bisdifluoromethoxyphenyl)-4-cyano-1-(3-methyl[1,2,4]oxadiazol-5-yl)cyclohexane};

cis-{4-(3,4-bisdifluoromethoxyphenyl)-4-cyano-1-(2-methyl[1,3,4]oxadiazol-5-yl)cyclohexane};

cis-{4-(3,4-bisdifluoromethoxyphenyl)-4-cyano-1-(2-methyl[1,3,4]thiadiazol-5-yl)cyclohexane };

cis-[4-cyano-4-(3-cyclopropylmethoxy-4-methoxyphenyl)-1-hydroxy-1-tris(methylthio)methylcyclohexane];

methyl cis-[4-cyano-4-(3-cyclopropylmethoxy-4-methoxyphenyl)-1-hydroxy-cyclohexane-1-carboxylate];

cis-[4-cyano-4-(3-cyclopropylmethoxy-4-methoxyphenyl)-1-hydroxycyclohexane-1-carboxylic acid];

cis-[4-cyano-4-(3-cyclopropylmethoxy-4-methoxyphenyl)-1-hydroxycyclohexane-1-carboxamide];

methyl cis-[4-cyano-4-(3-cyclopropylmethoxy-4-methoxyphenyl)-1-methoxy-cyclohexane-1-carboxylate];

cis-[4-cyano-4-(3-cyclopropylmethoxy-4-methoxyphenyl)-1-methoxycyclohexane-1-carboxylic acid];

cis-[4-cyano-4-(3-cyclopropylmethoxy-4-methoxyphenyl)-1-methoxycyclohexane-1-carboxamide];

trans-[4-cyano-4-(3-cyclopropylmethoxy-4-methoxyphenyl)-1-hydroxycyclohexane-1-carboxaldehyde];

methyl trans-[4-cyano-4-(3-cyclopropylmethoxy-4-methoxyphenyl)-1-hydroxycyclohexane-1-carboxylate];

trans-[4-cyano-4-(3-cyclopropylmethoxy-4-methoxyphenyl)-1-hydroxycyclohexane-1-carboxylic acid];

methyl trans-[4-cyano-4-(3-cyclopropylmethoxy-4-methoxyphenyl)-1-methoxycyclohexane-1-carboxylate];

trans-[4-cyano-4-(3-cyclopropylmethoxy-4-methoxyphenyl)-1-methoxycyclohexane-1-carboxylic acid];

trans-[4-cyano-4-(3-cyclopropylmethoxy-4-methoxyphenyl)-1-methoxycyclohexane-1-carboxamide];

cis-[4-cyano-4-(3-cyclopentyloxy-4-methoxyphenyl)cyclohexane-1-carboxamic acid];

N-methyl-cis-[4-cyano-4-(3-cyclopentyloxy-4-methoxyphenyl)cyclohexane-1-carboxamic acid];

cis-[4-cyano-4-(3-cyclopentyloxy-4-methoxyphenyl)cyclohexane-1-N-(2-cyanoethyl)carboxamide];

cis-[1-(2-cyanoethyl)-5-{4-cyano-4-(3-cyclopentyloxy-4-methoxyphenyl)cyclohexyl}tetrazole]; and cis-[4-cyano-4-(3-cyclopentyloxy-4-methoxyphenyl)-1-(tetrazol-5-yl)cyclohexane].

As regards the compounds of Formula (II), the preferred compounds are as follows:

When $R_1$ is an alkyl substituted by 1 or more halogens, the halogens are preferably fluorine and chlorine, more preferably a $C_{1-4}$ alkyl substituted by 1 or more fluorines. The preferred halo-substituted alkyl chain length is one or two carbons, and most preferred are the moieties —$CF_3$, —$CH_2F$, —$CHF_2$, —$CF_2CHF_2$, —$CH_2CF_3$, and —$CH_2CHF_2$. Preferred $R_1$ substitutents for the compounds of Formula (I) are $CH_2$-cyclopropyl, $CH_2$—$C_{5-6}$ cycloalkyl, $C_{4-6}$ cycloalkyl unsubstituted or substituted with OH$C_{7-11}$ polycycloalkyl, (3- or 4-cyclopentenyl), phenyl, tetrahydrofuran-3-yl, benzyl or $C_{1-2}$ alkyl unsubstituted or substituted by 1 or more fluorines, —$(CH_2)_{1-3}C(O)O(CH_2)_{0-2}CH_3$, —$(CH_2)_{1-3}O(CH_2)_{0-2}CH_3$, and —$(CH_2)_{2-4}OH$.

When $R_1$ term contains the moiety $(CR_4R_5)$, the $R_4$ and $R_5$ terms are independently hydrogen or alkyl. This allows for branching of the individual methylene units as $(CR_4R_5)_n$ or $(CR_4R_5)_m$; each repeating methylene unit is independent of the other, e.g., $(CR_4R_5)_n$ wherein n is 2 can be —$CH_2CH$(—$CH_3$)—, for instance. The individual hydrogen atoms of the repeating methylene unit or the branching hydrocarbon can unsubstituted or be substituted by fluorine independent of each other to yield, for instance, the preferred $R_1$ substitutions, as noted above.

When $R_1$ is a $C_{7-11}$ polycycloalkyl, examples are bicyclo[2.2.1]-heptyl, bicyclo[2.2.2]octyl, bicyclo[3.2.1]octyl, tricyclo[5.2.1.0$^{2,6}$]decyl, etc. additional examples of which are described in Saccamano et al., WO 87/06576, published Nov. 5, 1987.

W is preferably alkyl, alkenyl or alkynyl of 3 to 5 carbon atoms, and where it is alkenyl or alkynyl, that one or two double or triple bonds be present. It is most preferred that W is ethynyl or 1,3-butadiynyl.

Z is preferably $OR_{14}$, $OR_{15}$, $SR_{14}$, $S(O)_mR_7$, $S(O)_2NR_{10}R_{14}$, $NR_{10}R_{14}$, $NR_{14}C(O)R_9$, $NR_{10}C(O)R_{14}$, $NR_{10}C(O)OR_7$, $NR_{10}C(O)NR_{10}R_{14}$, $NR_{10}S(O)_2NR_{10}R_{14}$, $NR_{10}C(NCN)NR_{10}R_{14}$, $NR_{10}S(O)_2R_7$, $NR_{10}C(CR_4NO_2)NR_{10}R_{14}$, $NR_{10}C(NCN)SR_9$, $NR_{10}C(CR_4NO_2)SR_9$, $NR_{10}C(NR_{10})NR_{10}R_{14}$, $NR_{10}C(O)C(O)NR_{10}R_{14}$, or $NR_{10}C(O)C(O)OR_{14}$.

Preferred X groups for Formula (I) are those wherein X is $YR_2$ and Y is oxygen. The preferred $X_2$ group for Formula (Ia) is that wherein $X_2$ is oxygen. The preferred $X_3$ group for Formula (I) is that wherein $X_3$ is hydrogen. Preferred $R_2$ groups, where applicable, is a $C_{1-2}$ alkyl unsubstituted or substituted by 1 or more halogens. The halogen atoms are preferably fluorine and chlorine, more preferably fluorine. More preferred $R_2$ groups are those wherein $R_2$ is methyl, or the fluoro-substituted alkyls, specifically a $C_{1-2}$ alkyl, such as a —$CF_3$, —$CHF_2$, or —$CH_2CHF_2$ moiety. Most preferred are the —$CHF_2$ and —$CH_3$ moieties.

Preferred $R_7$ moieties include unsubstituted or substituted —$(CH_2)_{0-2}$(2-, 3- or 4-pyridyl), $(CH_2)_{1-2}$(2-imidazolyl), $(CH_2)_2$(4-morpholinyl), $(CH_2)_2$(4-piperazinyl), $(CH_2)_{1-2}$(2-thienyl), $(CH_2)_{1-2}$(4-thiazolyl), unsubstituted or substituted pyrimidinyl, and substituted or unsubstituted $(CH_2)_{0-2}$ phenyl.

Preferred rings when $R_{10}$ and $R_{11}$ in the moiety —$NR_{10}R_{11}$ together with the nitrogen to which they are attached form a 5 to 7 membered ring comprised of carbon or carbon and at least one heteroatom selected from O, N, or S include, but are not limited to 1-imidazolyl, 2-($R_8$)-1-imidazolyl, 1-pyrazolyl, 3-($R_8$)-1-pyrazolyl, 1-triazolyl, 2-triazolyl, 5-($R_8$)-1-triazolyl, 5-($R_8$)-2-triazoly 5-($R_8$)-1-tetrazolyl, 5-($R_8$)-2-tetrazolyl, 1-tetrazolyl, 2-tetrazloyl, morpholinyl, piperazinyl, 4-($R_8$)-1-piperazinyl, or pyrrolyl ring.

Preferred rings when $R_{10}$ and $R_{14}$ in the moiety —$NR_{10}R_{14}$ together with the nitrogen to which they are attached may form a 5 to 7 membered ring comprised of carbon or carbon and at least one heteroatom selected from O, N, or S include, but are not limited to 1-imidazolyl, 1-pyrazolyl, 1-triazolyl, 2-triazolyl, 1-tetrazolyl, 2-tetrazolyl, morpholinyl, piperazinyl, and pyrrolyl. The respective rings may be additionally substituted, where applicable, on an available nitrogen or carbon by the moiety $R_7$ as described herein for Formula (I). Illustrations of such carbon substitutions includes, but is not limited to, 2-($R_7$)-1-imidazolyl, 4-($R_7$)-1-imidazolyl, 5-($R_7$)-1-imidazolyl, 3-($R_7$)-1-pyrazolyl, 4-($R_7$)-1-pyrazolyl, 5-($R_7$)-1-pyrazolyl, 4-($R_7$)-2-triazolyl, 5-($R_7$)-2-triazolyl, 4-($R_7$)-1-triazolyl, 5-($R_7$)-1-triazolyl, 5-($R_7$)-1-tetrazolyl, and 5-($R_7$)-2-tetrazolyl. Applicable nitrogen substitution by $R_7$ includes, but is not limited to, 1-($R_7$)-2-tetrazolyl, 2-($R_7$)-1-tetrazolyl, 4-($R_7$)-1-piperazinyl. Where applicable, the ring may be substituted one or more times by $R_7$.

Preferred groups for $NR_{10}R_{14}$ which contain a heterocyclic ring are 5-($R_{14}$)-1-tetrazolyl, 2-($R_{14}$)-1-imidazolyl, 5-($R_{14}$)-2-tetrazolyl, 4-($R_{14}$)-1-piperazinyl, or 4-($R_{15}$)-1-piperazinyl.

Preferred rings for $R_{13}$ include (2-, 4- or 5-imidazolyl), (3-, 4- or 5-pyrazolyl), (4- or 5-triazolyl[1,2,3]), (3- or 5-triazolyl[1,2,4]), (5-tetrazolyl), (2-, 4- or 5-oxazolyl), (3-, 4- or 5-isoxazolyl), (3- or 5-oxadiazolyl[1,2,4]), (2-oxadiazolyl[1,3,4]), (2-thiadiazolyl[1,3,4]), (2-, 4-, or 5-thiazolyl), (2-, 4-, or 5-oxazolidinyl), (2-, 4-, or 5-thiazolidinyl), or (2-, 4-, or 5-imidazolidinyl).

When the $R_7$ group is unsubstituted or substituted by a heterocyclic ring such as imidazolyl, pyrazolyl, triazolyl, tetrazolyl, or thiazolyl, the heterocyclic ring itself may be unsubstituted or substituted by $R_8$ on an available nitrogen or carbon atom, such as 1-($R_8$)-2-imidazolyl, 1-($R_8$)-4-imidazolyl, 1-($R_8$)-5-imidazolyl, 1-($R_8$)-3-pyrazolyl, 1-($R_8$)-4-pyrazolyl, 1-($R_8$)-5-pyrazolyl, 1-($R_8$)-4-triazolyl, or 1-($R_8$)-5-triazolyl. Where applicable, the ring may be substituted one or more times by $R_8$.

Preferred are those compounds of Formula (II) wherein $R_1$ is —$CH_2$-cyclopropyl, —$CH_2$—$C_{5-6}$ cycloalkyl, —$C_{4-6}$ cycloalkyl unsubstituted or substituted by OH, tetrahydrofuran-3-yl, (3- or 4-cyclopentenyl), benzyl or —$C_{1-2}$ alkyl unsubstituted or substituted by 1 or more fluorines, and —$(CH_2)_{2-4}$ OH; $R_2$ is methyl or fluoro-substituted alkyl, W is ethynyl or 1,3-butadiynyl; $R_3$ is $R_7$ where $R_7$ is an unsubstituted or substituted aryl or heteroaryl ring, X is $YR_2$, and Z is $OR_{14}$, $OR_{15}$, $NR_{10}R_{14}$, or $NR_{14}C(O)R_9$.

Most preferred are those compounds of Formula (II) wherein $R_1$ is —$CH_2$-cyclopropyl, cyclopentyl, 3-hydroxycyclopentyl, methyl or $CF_2H$; X is $YR_2$; Y is oxygen; $X_2$ is oxygen; $X_3$ is hydrogen; and $R_2$ is $CF_2H$ or methyl, W is ethynyl or 1,3-butadiynyl, and $R_3$ is a substituted or unsubstituted pyrimidinyl ring.

The most preferred compounds of Formula (II) are:

cis-[4-(2-aminopyrimidin-5-ylethynyl)-4-(3-cyclopentyloxy-4-methoxyphenyl)cyclohexan-1-ol], cis-[4-(2-aminopyrimidin-4-ylethynyl)-4-(3-cyclopentyloxy-4-methoxyphenyl)-cyclohexan-1-ol], trans-[4-(2-acetamidopyrimidin-5-ylethynyl)-4-(3-cyclopentyloy-4-methoxyphenyl)cyclohexan-1-ol], trans-[4-(2-aminopyrmidin-5-yl-ethynyl)-4-(3-cyclopentyloxy-4-methoxyphenyl)-cyclohexan-1-ol, cis-[4-(2-methylaminopyrimidin-5-ylethynyl)-4-(3-cyclopentyloxy-4-methoxyphenyl)cyclohexan-1-ol], cis-[4-(3-cyclopentyloxy-4-methoxyphenyl)-4-(pyrid-4-ylethynyl)cyclohexan-1-ol], cis-[4-(3-cyclopentyloxy-4-methoxyphenyl)-4-(pyrid-2-ylethynyl)cyclohexan-1-ol], cis-[4-(4-cyanothien-2-ylethynyl)-4-(3-cyclopentyloxy-4-methoxyphenyl)cyclohexan-1-ol], cis-[4-(thiazol-2-ylethynyl)-4-(3-cyclopentyloxy-4-methoxyphenyl)cyclohexan-1-ol], cis-[4-(3-cyclopentyloxy-4-methoxyphenyl)-4-[4-(5-methyl-[1,2,4]oxadiazol-2-yl)thien-2-ylethynyl]cyclohexan-1-ol], cis-[4-(3-cyclopentyloxy-4-methoxyphenyl)-4-(2-[3-(3-methyl[1,2,4]oxadiazol-5-yl)phenyl]ethynyl)cyclohexan-1-ol], cis-[4-(3-cyclopentyloxy-4-methoxyphenyl)-4-(2-[3-(5-methyl[1,3,4]oxadiazol-2-yl)phenyl]ethynyl)cyclohexan-1-ol], cis-[4-(3-cyclopentyloxy-4-methoxyphenyl)-4-(2-[3-(5-methyl[1,2,4]oxadiazol-3-yl)phenyl]ethynyl)cyclohexan-1-ol], cis-4-(3-cyclopentyloxy-4-methoxyphenyl)-4-[3-(5-trifluoromethyl-[1,2,4]oxadiazol-3-yl)phenylethynyl)cyclohexan-1-ol, cis-4-(3-cyclopentyloxy-4-methoxyphenyl)-4-[3-(5-methyl-[1,3,4]thiadiazol-2-yl)phenylethynyl]cyclohexan-1-ol, trans-[4-(3-cyclopentyloxy-4-methoxyphenyl)-4-(pyrid-2-ylethynyl)cyclohexyl-1-amine], trans-[4-(3-cyclopentyloxy-4-methoxyphenyl)-4-(pyrid-2-ylethynyl)cyclohexyl-1-formarnide], trans-[4-(3-cyclopentyloxy-4-methoxyphenyl)-4-[5-(5-methyl-[1,2,4]oxadiazol-2-yl)thien-2-ylethynyl]cyclohexyl-1-amine], cyclohexylsulfamate salt cis-[4-(3-cyclopentyloxy-4-methoxyphenyl)-4-(pyrid-2-ylethynyl)cyclohexyl-1-amine], cis-[4-(3-cyclopentyloxy-4-methoxyphenyl)-4-(pyrid-2-ylethynyl)cyclohexyl-1-formamide], cis-[4-(3-cyclopentyloxy-4-methoxyphenyl)-4-[5-(5-methyl-[1,2,4]oxadiazol-2-yl)thien-2-ylethynyl]cyclohexyl-1-amine], cyclohexylsulfamate salt, trans-[4-(2-aminopyrimidin-5-ylethynyl)-4-(3-cyclopentyloxy-4-methoxyphenyl)cyclohexyl-1-amine], cyclohexylsulfamate salt, or cis-[4-(2-aminopyrimidin-5-ylethynyl)-4-(3-cyclopentyloxy-4-methoxyphenyl)cyclohexyl-1-amine], cyclohexylsulfamate salt.

Some compounds of Formula (I) and Formula (II) may exist in both racemic and optically active forms; some may also exist in distinct diastereomeric forms possessing distinct physical and biological properties. All of these compounds are considered to be within the scope of the present invention. Therefore another aspect of the present invention is the administration of either a racemate, a single enantiomeric form, a single diastereomeric form, or mixtures thereof.

The terms cis and trans denote stereochemistry at the C-1 position of the cyclohexane ring relative to the $R_3$ group at the C-4 position.

The terms "$C_{1-3}$ alkyl", "$C_{1-4}$ alkyl", "$C_{1-6}$ alkyl" or "alkyl" include both straight or branched chain radicals of 1 to 10, unless the chain length is limited thereto, including, but not limited to methyl, ethyl, n-propyl, isopropyl, n-butyl, sec-butyl, isobutyl, tert-butyl, and the like. "Alkenyl" includes both straight or branched chain radicals of 1 to 6 carbon lengths, unless the chain length is limited thereto, including but not limited to vinyl, 1-propenyl, 2-propenyl, 2-propynyl, or 3-methyl-2-propenyl. "Cycloalkyl" or "cycloalkyl alkyl" includes groups of 3–7 carbon atoms, such as cyclopropyl, cyclopropylmethyl, cyclopentyl, or cyclohexyl. "Aryl" or "aralkyl", unless specified otherwise, means an aromatic ring or ring system of 6–10 carbon atoms, such as phenyl, benzyl, phenethyl, or naphthyl. Preferably the aryl is monocyclic, i.e, phenyl. The alkyl chain includes both straight or branched chain radicals of 1 to 4 carbon atoms. "Heteroaryl" as used herein, is meant an aromatic ring system containing one or more heteroatoms, such as imidazolyl, triazolyl, oxazolyl, pyridyl, pyrimidyl, pyrazolyl, pyrrolyl, furanyl, or thienyl. "Halo" as used herein is meant all halogens, i.e., chloro, fluoro, bromo, or iodo.

Methods of Preparation

The preparation of compounds of Formula (I) is fully set forth in U.S. Pat. No. 5,552,438 issued Sep. 3, 1996. This patent is incorporated herein in its entirety by reference as if fully set out herein. The compounds of Formula (II) are known compound and can be prepared by the methods set out in published PCT application PCT/US95/16711 published as WO96/19988 on Jul. 4, 1996 or PCT/US96/08080 published as WO96/38150 on Dec. 5, 1996. The contents of these published PCT applications are incorporated herein by reference as if fully set forth herein.

Methods of Treatment

In order to use a compound of Formula (I) and (II) or a pharmaceutically acceptable salt thereof for the treatment of COPD, it will be formulated in accordance with standard pharmaceutical practice as a pharmaceutical composition. The compounds of Formula (I) and (II) or a pharmaceutically acceptable salt, polymorph, hydrate, etc., thereof can be used in the manufacture of a medicament for the prophylatic or therapeutic treatment of COPD.

The pharmaceutical composition of the present invention will comprise an effective, non-toxic amount of a compound of Formula (I) or (II) and a pharmaceutically acceptable carrier or diluent. The compounds of Formula (I) and (II) are administered in conventional dosage forms prepared by combining a compound of Formula (I) and (II) in an amount sufficient to reduce COPD symptoms and/or its progression, with standard pharmaceutical carriers according to conventional procedures. These procedures may involve mixing, granulating, and compressing or dissolving the ingredients as appropriate to the desired preparation.

Thus, if a solid carrier is used, the preparation can be tableted, placed in a hard gelatin capsule in powder or pellet form, or in the form of a troche or lozenge. The amount of solid carrier will vary widely but preferably will be from about 25 mg to about 1 gram. When a liquid carrier is used, the preparation will be in the form of a syrup, emulsion, soft gelatin capsule, sterile injectable liquid such as an ampule or nonaqueous liquid suspension. Where the composition is in the form of a capsule, any routine encapsulation is suitable, for example using the aforementioned carriers in a hard gelatin capsule shell. Where the composition is in the form of a soft gelatin shell capsule any pharmaceutical carrier routinely used for preparing dispersions or suspensions may be considered, for example aqueous gums, celluloses, silicates, or oils and are incorporated in a soft gelatin capsule shell. A syrup formulation will generally consist of a suspension or solution of the compound or salt in a liquid carrier for example, ethanol, glycerine, or water with a flavoring or coloring agent.

The daily dosage regimen for oral administration is suitably about 0.001 mg/kg to 100 mg/kg, preferably 0.01 mg/Kg to 40 mg/Kg, of a compound of Formula (I) and (II) or a pharmaceutically acceptable salt thereof calculated as the free base. The active ingredient may be administered from 1 to 6 times a day, sufficient to exhibit activity.

While it is possible for an active ingredient to be administered neat, it is preferable to present it as a pharmaceutical formulation. The active ingredient may comprise, for topical administration, from 0.001% to 10% w/w, e.g., from 1% to 2% by weight of formulation, although it may comprise as much as 10% w/w but preferably not in excess of 5% w/w and more preferably from 0.1% to 1% w/w of Formulation.

It will be recognized by one of skill in the art that the form and character of the pharmaceutically acceptable carrier or diluent is dictated by the amount of active ingredient with which it is to be combined, the route of administration, and other well-known variables.

Formulations of the present invention comprise an active ingredient together with one or more acceptable carrier(s) thereof and optionally any other therapeutic ingredient(s). The carrier(s) must be 'acceptable' in the sense of being compatible with the other ingredients of Formulation and not deleterious to the recipient thereof.

The preferred pharmaceutical formulation is an oral formulation and one which contains between about 1 mg and 60 mg of a compound of formula (I) or formula (II) at least once a day to a patient suffering from COPD or who is at risk for developing COPD. Perferably the formulation will be a tablet or similar solid dosage form such as an immediate release tablet. The more preferred formulation is a tablet which contains Formula (I) or Formula (II) in an amount of 5 mg, 10 mg, 15 mg or 20 mg. Most perferably the formulation will be an immediate release tablet which contain about 15 mg of a compound; perferably the compound will be cis-[4-cyano-4-(3-cyclopentyloxy-4-methoxyphenyl)cyclohexane-1-carboxylic acid]; or a pharmaceutically acceptable salt, polymorph, pro-drug, or hydrate thereof.

This invention relates to a method for treating COPD in a human suffering from COPD, or for preventing or reducing the intensity of the onset of COPD in a human, by administering at least once daily a pharmaceutical composition containing a compound of Formula (I) or Formula (II) in an amount between 1 mg and 20 mg admixed with a pharmaceutically acceptable excipient. More preferably the methods comprise administering a composition which contains 5 mg, 10 mg, 15 mg or 20 mg at least twice daily. Most preferably the compound will contain about 15 mg of cis-[4-cyano-4-(3-cyclopentyloxy-4-methoxyphenyl) cyclohexane-1-carboxylic acid]; or a pharmaceutically acceptable salt, polymorph, or hydrate thereof and will be administered twice daily. And perferably the composition will be administered as a tablet and will be administered orally.

EXAMPLE 1

Tablet Formulation

A tablet was prepared as described further herein using as the active ingredient cis-[4-cyano-4-(3-cyclopentyloxy-4-methoxyphenyl)cyclohexane-1-carboxylic acid] and the excipients listed in Table 1.

TABLE 1

| Ingredient | Quantity (mg/tablet) |
| --- | --- |
| cis-[4-cyano-4-(3-cyclopentyloxy-4-methoxyphenyl) cyclohexane-1-carboxylic acid]; | 15.0 |
| Lactose monohydrate | 103.0 |
| Microcrystalline cellulose | 70.0 |
| Sodium starch glycolate | 10.0 |
| Magnesium stearate | 2.0 |
| Opadry Yellow OY-S-22907 | 5.0 |
| Purified water purified water is removed by drying during the application of the coating suspension. | q.s. |
| AFC Tablet Weight | 205 |
| Tablet shape | octagonal |

The ingredients are separately weighed and screened. The active ingredient is mixed with lactose monohydrate, microcrystalline cellulose and sodium starch glycolate. Magnesium stearate is added to the mixture. The blend is compressed and the tablet cores are coated with an aqueous film coat.

Blending

Initial step: Weigh the acid, lactose, microcrystalline cellulose, sodium starch glycolate and magnesium stearate. Screen each ingredient to de-aggregate using a vibratory/shaker separator or equivalent, fitted with a suitable sieve screen.

Step 2: Charge a bin blender or equivalent with the microcrystalline cellulose, sodium starch glycolate, SB-207499 and lactose. Mix until a homogeneous blend is achieved (approximately 20 minutes).

Step 3: Add the magnesium stearate to the blender. Blend for approximately 3 minutes.

Compression and Coating

Step 1: Compress the tablets using a rotary tablet press or equivalent.

Step 2: Prepare a 12% w/w Opadry coating suspension, using 7.33 grams of purified water/gram of Opadry.

Step 3: Using a perforated pan coating system or equivalent, spray the coating suspension on the tablet cores until the desired tablet weight gain is obtained.

Step 4: Dry the tablets.

No toxic effects are expected when these compounds are administered in accordance with the present invention.

What is claimed is:

1. A method for treating COPD, which method comprises administering to a mammal suffering from COPD an effective amount of a compound of Formula (I):

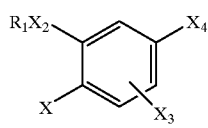

(I)

wherein:

$R_1$ is —$(CR_4R_5)_nC(O)O(CR_4R_5)_mR_6$, —$(CR_4R_5)_nC(O)NR_4(CR_4R_5)_mR_6$, —$(CR_4R_5)_nO(CR_4R_5)_mR_6$, or —$(CR_4R_5)_rR_6$ wherein the alkyl moieties may be optionally substituted with one or more halogens;

m is 0 to 2;

n is 1 to 4;

r is 0 to 6;

$R_4$ and $R_5$ are independently selected from hydrogen or a $C_{1-2}$ alkyl;

$R_6$ is $C_{3-6}$ cycloalkyl, or a $C_{4-6}$ cycloalkyl containing one or two unsaturated bonds, wherein the cycloalkyl moieties may be optionally substituted by OH, 1 to 3 methyl groups or one ethyl group;

X is $YR_2$, halogen, nitro, $NR_4R_5$, or formyl amine;

Y is O or $S(O)_{m'}$;

m' is 0, 1, or 2;

$X_2$ is O or $NR_8$;

$X_3$ is hydrogen or X;

$X_4$ is

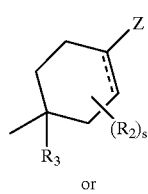

(a)

or

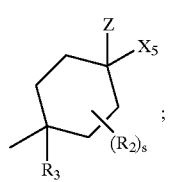

(b)

$X_5$ is H, $R_9$, $OR_8$, CN, $C(O)R_8$, $C(O)OR_8$, $C(O)NR_8R_8$, or $NR_8R_8$;

$R_2$ is independently selected from the group consisting of —$CH_3$ and —$CH_2CH_3$ optionally substituted by 1 or more halogens;

s is 0 to 4;

$R_3$ is CN;

Z is $C(Y')R_{14}$, $C(O)OR_{14}$, $C(Y')NR_{10}R_{14}$, $C(NR_{10})NR_{10}R_{14}$, CN, $C(NOR_8)R_{14}$, $C(O)NR_8NR_8C(O)R_8$, $C(O)NR_8NR_{10}R_{14}$, $C(NOR_{14})R_8$, $C(NR_8)NR_{10}R_{14}$, $C(NR_{14})NR_8R_8$ $C(NCN)NR_{10}R_{14}$, $C(NCN)SR_9$, (5-tetrazolyl), (3- or 5-oxadiazolyl[1,2,4]), (2-oxadiazolyl[1,3,4]), (2-thiadiazolyl[1,3,4]), wherein all of the heterocylic ring systems may be optionally substituted one or more times by $R_{14}$;

the dotted line in formula (a) optionally represents a single or double bond;

Y' is =O or =S;

$R_7$ is $(CR_4R_5)_qR_{12}$ or $C_{1-6}$ alkyl wherein the $R_{12}$ or $C_{1-6}$ alkyl group is optionally substituted one or more times by, —F, —Br, —Cl, —$NO_2$, —$NR_{10}R_{11}$, —$C(O)R_8$, —$C(O)OR_8$, —$OR_8$, —CN, —$C(O)NR_{10}R_{11}$, —$OC(O)NR_{10}R_{11}$, —$OC(O)R_8$, —$NR_{10}C(O)NR_{10}R_{11}$, —$NR_{10}C(O)R_{11}$, —$NR_{10}C(O)OR_9$, —$C(NR_{10})NR_{10}R_{11}$, —$C(NCN)NR_{10}R_{11}$, —$C(NCN)SR_9$, —$NR_{10}C(NCN)SR_9$, —$NR_{10}C(NCN)NR_{10}R_{11}$, —$NR_{10}S(O)_2R_9$, —$S(O)_m·R_9$, —$NR_{10}C(O)C(O)NR_{10}R_{11}$, —$NR_{10}C(O)C(O)R_{10}$, or wherein the $R_{12}$ or $C_{1-6}$ alkyl group is optionally substituted one or more times by $C_{1-2}$ alkyl optionally substituted by one to three fluorines;

q is 0, 1, or 2;

$R_{12}$ is $C_3$–$C_7$-cycloalkyl;

$R_8$ is independently selected from hydrogen or $R_9$;

$R_9$ is $C_{1-4}$ alkyl optionally substituted by one to three fluorines;

$R_{10}$ is $OR_8$ or $R_{11}$;

$R_{11}$ is hydrogen, or $C_{1-4}$ alkyl optionally substituted by one to three fluorines; or when $R_{10}$ and $R_{11}$ are as $NR_{10}R_{11}$ they may together with the nitrogen form in a 5 to 7 membered ring optionally containing at least one additional heteroatom selected from O/N/or S;

$R_{14}$ is hydrogen or $R_7$;

or the pharmaceutically acceptable salts thereof.

2. The method of claim 1 wherein in Formula (I) $R_1$ is —$CH_2$-cyclopropyl, cyclopentyl, methyl or $CF_2H$; $R_3$ is CN; X is $YR_2$; Y is oxygen; $X_2$ is oxygen; $X_3$ is hydrogen; and $R_2$ is $CF_2H$ or methyl.

3. The method of claim 2 wherein subject is a human and the compound is:

methyl 4-cyano-4-(3-cyclopentyloxy-4-methoxyphenyl)cyclohex-1-ene-1-carboxylate;

4-cyano-4-(3-cyclopentyloxy-4-methoxyphenyl)cyclohex-1-ene-1-carboxylic acid;

methyl cis-[4-cyano-4-(3-cyclopentyloxy-4-methoxyphenyl)cyclohexane-1-carboxylate];

methyl trans-[4-cyano-4-(3-cyclopentyloxy-4-methoxyphenyl)cyclohexane-1-carboxylate];

methyl cis-[4-(3,4-bisdifluoromethoxyphenyl)-4-cyanocyclohexane-1-carboxylate];

methyl trans-[4-(3,4-bisdifluoromethoxyphenyl)-4-cyanocyclohexane-1-carboxylate];

cis-[4-cyano-4-(3-cyclopentyloxy-4-methoxyphenyl)cyclohexane-1-carboxylate], tris(hydroxymethyl) ammonium methane salt;

cis-[4-(3,4-bisdifluoromethoxyphenyl)-4-cyanocyclohexane-1-carboxylic acid];

trans-[4-cyano-4-(3-cyclopentyloxy-4-methoxyphenyl) cyclohexane-1-carboxylic acid];
cis-[4-cyano-4-(3-cyclopropylmethoxy-4-methoxyphenyl, cyclohexane-1-carboxylic acid];
trans-[4-cyano-4-(3-cyclopropylmethoxy-4-methoxyphenyl)cyclohexane-1-carboxylic acid];
methyl cis-[4-cyano-4-(3-cyclopropylmethoxy-4-methoxyphenyl-cyclohexane-1-carboxylate];
methyl trans-[4-cyano-4-(3-cyclopropylmethoxy-4-methoxyphenyl)cyclohexane-1-carboxylate];
methyl cis-[4-cyano-4-(3-cyclopropylmethoxy-4-difluoromethoxyphenyl)cyclohexane-1-carboxylate];
methyl trans-[4-cyano-4-(3-cyclopropylmethoxy4-difluoromelhoxyphenyl)cyclohexane-1-carboxylate];
cis-[4-cyano-4-(3-cyclopropylmethoxy-4-difluoromethoxyphenyl)cyclohexane-1-carboxylic acid];
trans-[4-cyano-4-(3-cyclopropylmethoxy-4-difluoromethoxyphenyl)cyclohexane-1-carboxylic acid];
cis-[4-cyano-4-(3-cyclopentyloxy-4-methoxyphenyl) cyclohexane-1-carboxamide];
cis-[4-cyano-4-(3,4-bisdifluoromethoxyphenyl) cyclohexane-1-carboxamide];
trans-[4-cyano-4-(3,4-bisdifluoromethoxyphenyl) cyclohexane-1-carboxamide];
cis-[4-cyano-4-(3,4-bisdifluoromethoxyphenyl) cyclohexane-1-carbohydrazide];
cis-[4-cyano-4-(3,4-bisdifluoromethoxyphenyl) cyclohexane-1-(2-cetylcarbohydrazide)];
cis-{4-(3,4-bisdifluoromethoxyphenyl)-4-cyano-1-(3-methyl[1,2,4]oxadiazol-5-yl)cyclohexane};
cis-{4-(3,4-bisdifluoromethoxyphenyl)-4-cyano-1-(2-methyl[1,3,4]oxadiazol-5-yl)cyclohexane};
cis-{4-(3,4-bisdifluoromethoxyphenyl)-4-cyano-1-(2-methyl[1,3,4]thiadiazol-5-yl)cyclohexane};
cis-[4-cyano-4-(3-cyclopropylmethoxy-4-methoxyphenyl)-1-hydroxy-1-tris(methylthio)methyleyclohexane];
methyl cis-[4-cyano-4-(3-cyclopropylmethoxy-4-methoxyphenyl)-1-hydroxycyclohexane-1-carboxylate];
cis-[4-cyano-4-(3-cyclopropylmethoxy-4-methoxyphenyl)-1-hydroxycyclohexane-1-carboxylic acid];
cis-[4-cyano-4-(3-cyclopropylmethoxy-4-methoxyphenyl)-1-hydroxycyclohexane-1-carboxamide];
methyl cis-[4-cyano-4-(3-cyclopropylmethoxy-4-methoxyphenyl)-1-methoxycyclohexane-1-carboxylate];
cis-[4-cyano-4-(3-cyclopropyhnethoxy-4-methoxyphenyl)-1-metlhoxycyclohexane-1-carboxylic acid];
cis-[4-cyano-4-(3-cyclopropylmethoxy-4-methoxyphenyl)-1-methoxycyclohexane-1-carboxanide];
trans-[4-cyano-4-(3-cyclopropylmethoxy-4-methoxyphenyl)-1-hydroxy-cyclohexane-1-carboxaldehyde];
methyl trans-[4-cyano-4-(3-cyclopropylmethoxy-4-methoxyphenyl)-1-hydroxycyclohexane-1-carboxylate];
trans-[4-cyano-4-(3-cyclopropylmethoxy-4-methoxyphenyl)-1-hydroxycyclohexane-1-carboxylic acid];
methyl trans-[4-cyano-4-(3-cyclopropylmethoxy-4-methoxyphenyl)-1-methoxycyclohexane-1-carboxylate];
trans-[4-cyano-4-(3-cyclopropylmethoxy-4-methoxyphenyl)-1-methoxycyclohexane-1-carboxylic acid];
trans-[4-cyano-4-(3-cyclopropylmethoxy-4-methoxyphenyl)-1-methoxycyclohexane-1-carboxamide];
cis-[4-cyano-4-(3-cyclopentyloxy-4-methoxyphenyl) cyclohexane-1-carboxamic acid];
N-methyl-cis-[4-cyano-4-(3-cyclopentyloxy-4-methoxyphenyl)cyclohexane-1-carboxamic acid];
cis-[4-cyano-4-(3-cyclopentyloxy-4-methoxyphenyl) cyclohexane-1-N-(2-cyanoethyl)carboxamide];
cis-[1-(2-cyanoethyl)-5-{4-cyano-4-(3-cyclopentyloxy-4-methoxyphenyl)cyclohexyl}tetrazole]; or
cis-[4-cyano-4-(3-cyclopentyloxy-4-methoxyphenyl)-1-(tetrazol-5-yl)cyclohexane].

4. The method of claim 1 wherein the subject is a human and the compound is cis-[4-cyano-4(3-cyclopentyloxy-4-methoxyphenyl)cyclohexane-1-carboxylic acid or a pharmaceutically acceptable salt or ester thereof.

5. The method of claim 4 wherein the compound is administered at least twice daily.

6. The method of claim 5 wherein the compound is administered twice daily and at each time is administered in an amount between 1 mg and 20 mg.

7. The method of claim 6 wherein the amount of compound administered at each time is 15 mg, is in tablet form and is administered orally.

8. A method for the phrophylatic treatment of a mammal at risk for developing COPD, said method comprising administering a composition comprising a compound of Formula (I) in an amount between 1 and 60 mg admixed with a pharmaceutically acceptable excipient at least once daily, wherein Formula (I) comprises:

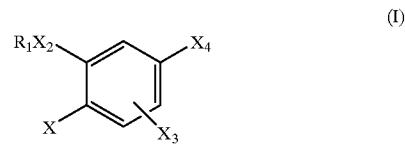

(I)

wherein:

$R_1$ is —$(CR_4R_5)_nC(O)O(CR_4R_5)_mR_6$, —$(CR_4R_5)_nC(O)NR_4(CR_4R_5)_mR_6$, —$(CR_4R_5)_mO(CR_4R_5)_mR_6$, or —$(CR_4R_5)_rR_6$ wherein the alkyl moieties may be optionally substituted with one or more halogens;

m is 0 to 2;

n is 1 to 4;

r is 0 to 6;

$R_4$ and $R_5$ are independently selected from hydrogen or a $C_{1-2}$ alkyl;

$R_6$ is $C_{3-6}$ cycloalkyl, or a $C_{4-6}$ cycloalkyl containing one or two unsaturated bonds, wherein the cycloalkyl moieties may be optionally substituted by OH, 1 to 3 methyl groups or one ethyl group;

X is $YR_2$, halogen, nitro, $NR_4R_5$, or formyl amine;

Y is O or $S(O)_{m'}$;

m' is 0, 1, or 2;

$X_2$ is O or $NR_8$;

$X_3$ is hydrogen or X;

$X_4$ is

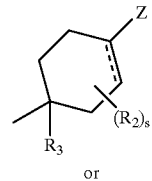

(a)

or

-continued (b)

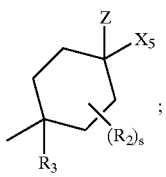

X$_5$ is H, R$_9$, OR$_8$, CN, C(O)R$_8$, C(O)OR$_8$, C(O)NR$_8$R$_8$, or NR$_8$R$_8$;

R$_2$ is independently selected from the group consisting of —CH$_3$ and —CH$_2$CH$_3$ optionally substituted by 1 or more halogens;

s is 0 to 4;

R$_3$ is CN;

Z is C(Y')R$_{14}$, C(O)OR$_{14}$, C(Y')NR$_{10}$R$_{14}$, C(NR$_{10}$)NR$_{10}$R$_{14}$, CN, C(NOR$_8$)R$_{14}$, C(O)NR$_8$NR$_8$C(O)R$_8$, C(O)NR$_8$NR$_{10}$R$_{14}$, C(NOR$_{14}$)R$_8$, C(NR$_8$)NR$_{10}$R$_{14}$, C(NR$_{14}$)NR$_8$R$_8$, C(NCN)NR$_{10}$R$_{14}$, C(NCN)SR$_9$, (5-tetrazolyl), (3- or 5-oxadiazolyl[1,2,4]), (2-oxadiazolyl[1,3,4]), (2-thiadiazolyl[1,3,4]), wherein all of the heterocylic ring systems may be optionally substituted one or more times by R$_{14}$;

the dotted line in formula (a) optionally represents a single or double bond;

Y' is O or S;

R$_7$ is —(CR$_4$R$_5$)$_q$R$^{12}$ or C$_{1-6}$ alkyl wherein the R$_{12}$ or C$_{1-6}$ alkyl group is optionally substituted one or more times by —F, —Br, —Cl, —NO$_2$, —NR$_{10}$R$_{11}$, —C(O)R$_8$, —C(O)OR$_8$, —OR$_8$, —CN, —C(O)NR$_{10}$R$_{11}$, —OC(O)NR$_{10}$R$_{11}$, —OC(O)R$_8$, —NR$_{10}$C(O)NR$_{10}$R$_{11}$, —NR$_{10}$C(O)R$_{11}$, —NR$_{10}$C(O)OR$_9$, —C(NR$_{10}$)NR$_{10}$R$_{11}$, —C(NCN)NR$_{10}$R$_{11}$, —C(NCN)SR$_9$, —NR$_{10}$C(NCN)SR$_9$, —NR$_{10}$C(NCN)NR$_{10}$R$_{11}$, —NR$_{10}$S(O)$_2$R$_9$, —S(O)$_m$R$_9$, —NR$_{10}$C(O)C(O)NR$_{10}$R$_{11}$, —NR$_{10}$C(O)C(O)R$_{10}$, or wherein the R$_{12}$ or C$_{1-6}$ alkyl group is optionally substituted one or more times by C$_{1-2}$ alkyl optionally substituted by one to three fluorines;

q is 0, 1, or 2;

R$_{12}$ is C$_{3-7}$ cycloalkyl,;

R$_8$ is independently selected from hydrogen or R$_9$;

R$_9$ is C$_{1-4}$ alkyl optionally substituted by one to three fluorines;

R$_{10}$ is OR$_8$ or R$_{11}$;

R$_{11}$ is hydrogen, or C$_{1-4}$ alkyl optionally substituted by one to three fluorines; or when R$_{10}$ and R$_{11}$ are as NR$_{10}$R$_{11}$ they may together with the nitrogen form a 5 to 7 membered ring optionally containing at least one additional heteroatom selected from O, N, or S;

R$_{14}$ is hydrogen or R$_7$;

or the pharmaceutically acceptable salts thereof.

9. The method of claim 8 wherein in Formula (I) R$_1$ is —CH$_2$-cyclopropyl, cyclopentyl, methyl or CF$_2$H; R$_3$ is CN; X is YR$_2$; Y is oxygen; X$_2$ is oxygen; X$_3$ is hydrogen; and R$_2$ is CF$_2$H or methyl.

10. The method of claim 9 wherein the subject is a human and the compound is methyl 4-cyano-4-(3-cyclopentyloxy-4-methoxyphenyl)cyclohex-1-ene-1-carboxylate;
4-cyano-4-(3-cyclopentyloxy-4-methoxyphenyl)cyclohex-1-ene-1-carboxylic acid;
methyl cis-[4-cyano-4-(3-cyclopentyloxy-4-methoxyphenyl)cyclohexane-1-carboxylate];
methyl trans-[4-cyano-4-(3-cyclopentyloxy-4-methoxyphenyl)cyclohexane-1-carboxylate];
methyl cis-[4-(3,4-bisdifluoromethoxyphenyl)-4-cyanocyclohexane-1-carboxylate];
methyl trans-[4-(3,4-bisdifluoromethoxyphenyl)-4-cyanocyclohexane-1-carboxylate];
cis-[4-cyano-4-(3-cyclopentyloxy-4-methoxyphenyl)cyclohexane-1-carboxylate], tris(hydroxymethyl) ammonium methane salt;
cis-[4-(3,4-bisdifluoromethoxyphenyl)-4-cyanocyclohexane-1-carboxylic acid];
trans-[4-cyano-4-(3-cyclopentyloxy-4-methoxyphenyl)cyclohexane-1-carboxylic acid];
cis-[4-cyano-4-(3-cyclopropylmethoxy-4-methoxyphenyl)cyclohexane-1-carboxylic acid];
trans-[4-cyano-4-(3-cyclopropylmethoxy-4-methoxyphenyl)cyclohexane-1-carboxylic acid];
methyl cis-[4-cyano-4-(3-cyclopropylmethoxy-4-methoxyphenyl)cyclohexane-1-carboxylate];
methyl trans-[4-cyano-4-(3-cyclopropylmethoxy-4-methoxyphenyl)cyclohexane-1-carboxylate];
methyl cis-[4-cyano-4-(3-cyclopropylmethoxy-4-ifluoromethoxyphenyl)cyclohexane-1-carboxylate];
methyl trans-[4-cyano-4-(3-cyclopropylmethoxy-4-difluoromethoxyphenyl)cyclohexane-1-carboxylate];
cis-[4-cyano-4-(3-cyclopropylmethoxy-4-difluoromethoxyphenyl)cyclohexane-1-carboxylic acid];
trans-[4-cyano-4-(3-cyclopropylmethoxy-4-difluoromethoxyphenyl)cyclohexane-1-carboxylic acid];
cis-[4-cyano-4-(3-cyclopentyloxy-4-methoxyphenyl)cyclohexane-1-carboxamide];
cis-[4-cyano-4-(3,4-bisdifluoromethoxyphenyl)cyclohexane-1-carboxamide];
trans-[4-cyano-4-(3,4-bisdifluoromethoxyphenyl)cyclohexane-1-carboxamide];
cis-[4-cyano-4-(3,4-bisdifluoromethoxyphenyl)cyclohexane-1-carbohydrazide];
cis-[4-cyano-4-(3,4-bisdifluoromethoxyphenyl)cyclohexane-1-(2-cetylcarbohydrazide)];
cis-{4-(3,4-bisdifluoromethoxyphenyl)-4-cyano-1-(3-methyl[1,2,4]oxadiazol-5-yl)cyclohexane};
cis-{4-(3,4-bisdifluloromethoxyphenyl)-4-cyano-1-(2-methyl[1,3,4]oxadiazol-5-yl)cyclohexane};
cis-{4-(3,4-bisdifluoromethoxyphenyl)-4-cyano-1-(2-methyl[1,3,4]thiadiazol-5-yl)cyclohexane};
cis-[4-cyano-4-(3-cyclopropylmethoxy-4-methoxyphenyl)-1-hydroxy-1-tris(methylthio)methylcyclohexane];
methyl cis-[4-cyano-4-(3-cyclopropylmethoxy-4-methoxyphenyl)-1-hydroxycyclohexane-1-carboxylate];
cis-[4-cyano-4-(3-cyclopropylmethoxy-4-methoxyphenyl)-1-hydroxycyclohexane-1-carboxylic acid]; SB 208970
cis-[4-cyano-4-(3-cyclopropylmethoxy-4-methoxyphenyl)-1-hydroxycyclohexane-1-carboxanmide];
methyl cis-[4-cyano-4-(3-cyclopropylmethoxy-4-methoxyphenyl)-1-methoxycyclohexane-1-carboxylate];
cis-[4-cyano-4-(3-cyclopropylmethoxy-4-methoxyphenyl)-1-methoxycyclohexane-1-carboxylic acid];
cis-[4-cyano-4-(3-cyclopropylmethoxy-4-methoxyphenyl)-1-methoxycyclohexane-1-carboxamide];
trans-[4-cyano-4-(3-cyclopropylmethoxy-4-methoxyphenyl)-1-hydroxy-cyclohexane-1-carboxaldehyde];
methyl trans-[4-cyano-4-(3-cyclopropylmethoxy-4-methoxyphenyl)-1-hydroxycyclohexane-1-carboxylate];
trans-[4-cyano-4-(3-cyclopropylmethoxy-4-methoxyphenyl)-1-hydroxycyclohexane-1-carboxylic acid];

methyl trans-[4-cyano-4-(3-cyclopropylmethoxy-4-methoxyphenyl)-1-methoxycyclohexane-1-carboxylate];

trans-[4-cyano-4-(3-cyclopropylmethoxy-4-methoxyphenyl)-1-methoxycyclohexane-1-carboxylic acid];

trans-[4-cyano-4-(3-cyclopropylmethoxy-4-methoxyphenyl)-1-methoxycyclohexane-1-carboxamide];

cis-[4-cyano-4-(3-cyclopentyloxy-4-methoxyphenyl)cyclohexane-1-carboxamic acid];

N-methyl-cis-[4-cyano-4-(3-cyclopentyloxy-4-methoxyphenyl)cyclohexane-1-carboxamic acid];

cis-[4-cyano-4-(3-cyclopentyloxy-4-methoxyphenyl)cyclohexane-1-N-(2-cyanoetlhyl)carboxamide];

cis-[1-(2-cyanoethyl)-5-{4-cyano-4-(3-cyclopentyloxy-4-methoxyphenyl)cyclohexyl}tetrazole]; or cis-[4-cyano-4-(3-cyclopentyloxy-4-methoxyphenyl)-1-(tetrazol-5-yl)cyclohexane].

11. The method of claim 9 wherein the subject is a human and the compound is cis-[4-cyano-4-(3-cyclopentyloxy-4-methoxyphenyl)cyclohexane-1-carboxylic acid or a pharmaceutically acceptable salt or ester thereof.

12. The method of claim 9 wherein the compound is administered at least twice daily and at each time is administered in an amount between 1 mg and 20 mg.

13. The method of claim 9 wherein the compound is administered twice daily and at each time is administered in an amount between 1 mg and 20 mg.

14. The method of claim 13 wherein the amount of compound administered at each time is 15 mg, is in tablet form, and is administered orally.

* * * * *